(12) United States Patent
Kleiner

(10) Patent No.: US 9,826,988 B2
(45) Date of Patent: *Nov. 28, 2017

(54) DEVICES AND METHODS FOR PREPARING AN INTERVERTEBRAL WORKSPACE

(71) Applicant: Kleiner Intellectual Property, LLC, Denver, CO (US)

(72) Inventor: Jeffrey Kleiner, Denver, CO (US)

(73) Assignee: Kleiner Intellectual Property, LLC, Denver, CO (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/010,611

(22) Filed: Jan. 29, 2016

(65) Prior Publication Data

US 2016/0166261 A1 Jun. 16, 2016

Related U.S. Application Data

(63) Continuation of application No. 13/168,611, filed on Jun. 24, 2011, now Pat. No. 9,247,943, which is a
(Continued)

(51) Int. Cl.
*A61B 17/16* (2006.01)
*A61B 17/17* (2006.01)

(52) U.S. Cl.
CPC ...... *A61B 17/1659* (2013.01); *A61B 17/1644* (2013.01); *A61B 17/1671* (2013.01);
(Continued)

(58) Field of Classification Search
CPC .. A61B 17/17; A61B 17/1659; A61B 17/1671
See application file for complete search history.

(56) References Cited

U.S. PATENT DOCUMENTS

| D30,951 S | 6/1899 | Saint Cyr, Jr. |
| 1,867,624 A | 7/1932 | Hoffman |

(Continued)

FOREIGN PATENT DOCUMENTS

| FR | 2790946 | 9/2000 |
| JP | H09-327468 | 12/1997 |

(Continued)

OTHER PUBLICATIONS

U.S. Appl. No. 14/214,031, filed Mar. 14, 2014, Greenhalgh.
(Continued)

*Primary Examiner* — Christopher Beccia
(74) *Attorney, Agent, or Firm* — Sheridan Ross P.C.

(57) ABSTRACT

Tools adapted for spinal distraction are provided. More specifically, tools having an elongate shaft connected to a head portion are provided for imparting a force for displacing vertebral bodies. The tools may comprise features, such as textured surfaces or the ability to transmit pressure, for cleaning and preparing a spinal disc space for subsequent tools and procedures. A plurality or set of distraction tools is contemplated where the plurality of tools is made up of tools having various distinctions from one another. Such distinctions may be in the way of length, width, angle, and other geometric features or may comprise differences in materials or additional features.

20 Claims, 9 Drawing Sheets

Related U.S. Application Data continuation-in-part of application No. 12/367,487, filed on Feb. 6, 2009, now Pat. No. 8,088,163.

(60) Provisional application No. 61/358,149, filed on Jun. 24, 2010.

(52) U.S. Cl.
CPC .... *A61B 17/1757* (2013.01); *A61B 2217/005* (2013.01); *A61B 2217/007* (2013.01); *A61B 2218/002* (2013.01); *A61B 2218/007* (2013.01)

(56) References Cited

U.S. PATENT DOCUMENTS

| | | |
|---|---|---|
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A | 7/1981 | Solomon |
| 4,338,925 A | 7/1982 | Miller |
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,739,750 A | 4/1988 | Masse et al. |
| 4,743,256 A | 5/1988 | Brantigan |
| 4,863,476 A | 9/1989 | Shepperd |
| 4,877,399 A | 10/1989 | Frank et al. |
| 4,925,924 A | 5/1990 | Silver et al. |
| D309,499 S | 7/1990 | Bowman et al. |
| D312,309 S | 11/1990 | Michelson |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,122,130 A | 6/1992 | Keller |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| 5,425,772 A | 6/1995 | Brantigan |
| D360,689 S | 7/1995 | Giampapa |
| 5,431,658 A | 7/1995 | Moskovich |
| 5,443,514 A | 8/1995 | Steffee |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| 5,531,749 A | 7/1996 | Michelson |
| D372,781 S | 8/1996 | Reif |
| 5,549,607 A | 8/1996 | Olson et al. |
| 5,554,191 A | 9/1996 | Lahille et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,683,464 A | 11/1997 | Wagner et al. |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,752,969 A | 5/1998 | Cunci et al. |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A * | 7/1999 | Thomas ............. A61B 17/1615 606/170 |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,989,289 A | 11/1999 | Coates et al. |
| 5,997,895 A | 12/1999 | Narotam et al. |
| 6,004,191 A | 12/1999 | Schur et al. |
| 6,004,326 A | 12/1999 | Castro et al. |
| 6,008,433 A | 12/1999 | Stone |
| 6,013,028 A | 1/2000 | Jho et al. |
| 6,019,765 A | 2/2000 | Thornhill et al. |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,059,829 A | 5/2000 | Schlapfer et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,123,705 A | 9/2000 | Michelson |
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,180,085 B1 | 1/2001 | Achilefu |
| 6,200,322 B1 | 3/2001 | Branch et al. |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,224,607 B1 | 5/2001 | Michelson |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| D444,878 S | 7/2001 | Walter |
| D445,188 S | 7/2001 | Walter |

(56) References Cited

U.S. PATENT DOCUMENTS

| | | |
|---|---|---|
| 6,258,094 B1 | 7/2001 | Nicholson et al. |
| 6,258,125 B1 | 7/2001 | Paul et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |
| 6,309,395 B1 | 10/2001 | Smith et al. |
| 1,632,873 A1 | 12/2001 | Suddaby |
| 6,325,805 B1 | 12/2001 | Ogilvie et al. |
| 6,336,928 B1 | 1/2002 | Guerin et al. |
| 6,342,074 B1 | 1/2002 | Simpson |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,416,551 B1 | 7/2002 | Keller |
| 6,436,101 B1 | 8/2002 | Hamada |
| 6,451,017 B1 | 9/2002 | Moutafis et al. |
| 6,454,806 B1 | 9/2002 | Cohen et al. |
| 6,467,556 B2 | 10/2002 | Alsruhe |
| D467,657 S | 12/2002 | Scribner |
| 6,500,206 B1 | 12/2002 | Bryan |
| 6,511,493 B1 | 1/2003 | Moutafis et al. |
| D469,871 S | 2/2003 | Sand |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,613,091 B1 | 9/2003 | Zdeblick et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,723,096 B1 | 4/2004 | Dorchak et al. |
| 6,723,126 B2 | 4/2004 | Berry |
| 6,730,125 B1 | 5/2004 | Lin |
| 6,743,255 B2 | 6/2004 | Ferree |
| 6,743,257 B2 | 6/2004 | Castro |
| 6,746,487 B2 | 6/2004 | Scifert et al. |
| 6,764,491 B2 | 7/2004 | Frey et al. |
| 6,770,074 B2 | 8/2004 | Michelson |
| 6,773,437 B2 | 8/2004 | Ogilvie et al. |
| 6,773,460 B2 | 8/2004 | Jackson |
| 6,800,093 B2 | 10/2004 | Nicholson et al. |
| 6,823,871 B2 | 11/2004 | Schmieding |
| 6,824,565 B2 | 11/2004 | Muhanna et al. |
| 6,830,574 B2 | 12/2004 | Heckele et al. |
| 6,835,206 B2 | 12/2004 | Jackson |
| 6,852,126 B2 | 2/2005 | Ahlgren |
| 6,869,430 B2 | 3/2005 | Balbierz et al. |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,923,814 B2 | 8/2005 | Hildebrand et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,972,035 B2 | 12/2005 | Michelson |
| 6,974,480 B2 | 12/2005 | Messerli et al. |
| 6,991,653 B2 | 1/2006 | White et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,041,137 B2 | 5/2006 | Fulton et al. |
| 7,066,961 B2 | 6/2006 | Hichelson |
| D524,443 S | 7/2006 | Blain |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,169,182 B2 | 1/2007 | Errico et al. |
| 7,182,782 B2 | 2/2007 | Kirschman |
| 7,204,825 B2 | 4/2007 | Cimino et al. |
| 7,207,992 B2 | 4/2007 | Ritland |
| D541,940 S | 5/2007 | Blain |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| D582,552 S | 12/2008 | Berberich |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,553,320 B2 | 6/2009 | Molz, IV et al. |
| D597,669 S | 8/2009 | Petersen |
| D598,096 S | 8/2009 | Petersen |
| D599,015 S | 8/2009 | Petersen |
| 7,578,820 B2 | 8/2009 | Moore et al. |
| D600,806 S | 9/2009 | Horton et al. |

(56) References Cited

U.S. PATENT DOCUMENTS

| | | |
|---|---|---|
| D601,251 S | 9/2009 | Horton et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,625,374 B2 | 12/2009 | Branch et al. |
| 7,632,276 B2 | 12/2009 | Fishbein |
| 7,632,281 B2 | 12/2009 | Errico et al. |
| D608,001 S | 1/2010 | Reardon et al. |
| 7,655,027 B2 | 2/2010 | Michelson |
| 7,658,766 B2 | 2/2010 | Melkent et al. |
| D611,147 S | 3/2010 | Hanson et al. |
| 7,671,014 B2 | 3/2010 | Beals et al. |
| 7,674,265 B2 | 3/2010 | Smith et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| D615,653 S | 5/2010 | Horton |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,723,291 B2 | 5/2010 | Beals et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella et al. |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Lott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,473 B2 | 8/2010 | Thramann |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| D623,748 S | 9/2010 | Horton et al. |
| D623,749 S | 9/2010 | Horton et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,803,159 B2 | 9/2010 | Perez-Cruet et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| 7,819,921 B2 | 10/2010 | Grotz |
| D627,460 S | 11/2010 | Horton |
| D627,468 S | 11/2010 | Richter et al. |
| 7,824,328 B2 | 11/2010 | Gattani et al. |
| 7,824,332 B2 | 11/2010 | Fakhrai |
| 7,824,410 B2 | 11/2010 | Simonson |
| 7,824,703 B2 | 11/2010 | Scifert et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| D628,694 S | 12/2010 | Donnez |
| D629,896 S | 12/2010 | Horton |
| 7,846,210 B2 | 12/2010 | Perez-Cruet et al. |
| 7,850,733 B2 | 12/2010 | Baynham et al. |
| 7,850,735 B2 | 12/2010 | Eisermann et al. |
| 7,850,736 B2 | 12/2010 | Heinz et al. |
| D631,156 S | 1/2011 | Halder et al. |
| 7,867,277 B1 | 1/2011 | Tohmeh |
| D631,967 S | 2/2011 | Horton |
| 7,892,261 B2 | 2/2011 | Bonutti |
| 7,897,164 B2 | 3/2011 | Scifert |
| 7,897,564 B2 | 3/2011 | Beals et al. |
| 7,905,840 B2 | 3/2011 | Pimenta et al. |
| 7,905,886 B1 | 3/2011 | Curran et al. |
| 7,918,891 B1 | 4/2011 | Curran et al. |
| 7,922,766 B2 | 4/2011 | Grob et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,951,107 B2 | 5/2011 | Staid et al. |
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,985,256 B2 | 7/2011 | Grotz et al. |
| D643,921 S | 8/2011 | Davila |
| D647,202 S | 10/2011 | Scifert |
| D650,481 S | 12/2011 | Gottlieb et al. |
| 8,080,521 B2 | 12/2011 | Beals et al. |
| 8,088,163 B1 | 1/2012 | Kleiner |
| D653,757 S | 2/2012 | Binder |
| D655,414 S | 3/2012 | Cuschieri et al. |

(56) References Cited

U.S. PATENT DOCUMENTS

| | | |
|---|---|---|
| D656,610 S | 3/2012 | Kleiner |
| 8,148,326 B2 | 4/2012 | Beals et al. |
| D660,428 S | 5/2012 | Hohl |
| 8,198,238 B2 | 6/2012 | Beals et al. |
| 8,246,572 B2 | 8/2012 | Cantor et al. |
| D667,542 S | 9/2012 | Kleiner |
| 8,273,129 B2 | 9/2012 | Baynham et al. |
| 8,277,510 B2 | 10/2012 | Kleiner |
| 8,282,683 B2 | 10/2012 | McLaughlin et al. |
| 8,292,960 B2 | 10/2012 | Kleiner |
| 8,293,232 B2 | 10/2012 | Beals et al. |
| 8,303,659 B2 | 11/2012 | Errico et al. |
| D674,900 S | 1/2013 | Janice et al. |
| 8,361,152 B2 | 1/2013 | McCormack et al. |
| 8,366,748 B2 | 2/2013 | Kleiner |
| D677,791 S | 3/2013 | Danacioglu et al. |
| 8,394,129 B2 | 3/2013 | Morgenstern Lopez et al. |
| D681,205 S | 4/2013 | Farris et al. |
| 8,454,621 B2 | 6/2013 | DeRidder et al. |
| 8,506,635 B2 | 8/2013 | Palmatier et al. |
| 8,512,347 B2 | 8/2013 | McCormack et al. |
| 8,518,087 B2 | 8/2013 | Lopez et al. |
| D692,133 S | 10/2013 | Steinwachs et al. |
| 8,556,979 B2 | 10/2013 | Glerum et al. |
| 8,562,685 B2 | 10/2013 | Ullrich, Jr. et al. |
| 8,585,761 B2 | 11/2013 | Theofilos |
| 8,591,585 B2 | 11/2013 | McLaughlin et al. |
| D696,399 S | 12/2013 | Kleiner |
| 8,597,333 B2 | 12/2013 | Morgenstern Lopez et al. |
| 8,623,054 B2 | 1/2014 | McCormack et al. |
| 8,628,576 B2 | 1/2014 | Triplett et al. |
| D700,322 S | 2/2014 | Kleiner |
| D700,332 S | 2/2014 | Tyber |
| 8,685,031 B2 | 4/2014 | Kleiner |
| 8,709,086 B2 | 4/2014 | Glerum |
| 8,709,088 B2 | 4/2014 | Kleiner et al. |
| 8,715,351 B1 | 5/2014 | Pinto |
| 8,753,345 B2 | 6/2014 | McCormack et al. |
| 8,753,347 B2 | 6/2014 | McCormack et al. |
| 8,753,377 B2 | 6/2014 | McCormack et al. |
| 8,758,443 B2 | 6/2014 | Ullrich, Jr. et al. |
| D708,323 S | 7/2014 | Reyes et al. |
| D708,747 S | 7/2014 | Curran et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,304 B2 | 8/2014 | Weiman et al. |
| 8,808,305 B2 | 8/2014 | Kleiner |
| 8,808,383 B2 | 8/2014 | Kwak et al. |
| 8,814,940 B2 | 8/2014 | Curran et al. |
| 8,821,396 B1 | 9/2014 | Miles et al. |
| 8,828,019 B1 | 9/2014 | Raymond et al. |
| 8,828,062 B2 | 9/2014 | McCormack et al. |
| 8,834,472 B2 | 9/2014 | McCormack et al. |
| 8,840,622 B1 | 9/2014 | Vellido et al. |
| 8,840,668 B1 | 9/2014 | Donahoe et al. |
| 8,845,727 B2 | 9/2014 | Gottlieb et al. |
| 8,845,731 B2 | 9/2014 | Weiman |
| 8,845,732 B2 | 9/2014 | Weiman |
| 8,845,734 B2 | 9/2014 | Weiman |
| D714,933 S | 10/2014 | Kawamura |
| 8,852,242 B2 | 10/2014 | Morgenstern Lopez et al. |
| 8,852,243 B2 | 10/2014 | Morgenstern Lopez et al. |
| 8,852,244 B2 | 10/2014 | Simonson |
| 8,852,279 B2 | 10/2014 | Weiman |
| 8,852,281 B2 | 10/2014 | Phelps |
| 8,852,282 B2 | 10/2014 | Farley et al. |
| 8,858,598 B2 | 10/2014 | Seifert et al. |
| 8,870,882 B2 | 10/2014 | Kleiner |
| 8,906,028 B2 | 12/2014 | Kleiner |
| D721,808 S | 1/2015 | Oi |
| 8,932,295 B1 | 1/2015 | Greenhalgh |
| 8,945,137 B1 | 2/2015 | Greenhalgh et al. |
| D723,682 S | 3/2015 | Kleiner |
| D724,213 S | 3/2015 | Tyber |
| 8,992,622 B2 | 3/2015 | Ullrich, Jr. et al. |
| 9,060,877 B2 | 6/2015 | Kleiner |
| D735,336 S | 7/2015 | Lovell |
| 9,173,694 B2 | 11/2015 | Kleiner |
| 9,186,193 B2 | 11/2015 | Kleiner et al. |
| D750,249 S | 2/2016 | Grimber et al. |
| 9,247,943 B1 | 2/2016 | Kleiner |
| 9,427,264 B2 | 8/2016 | Kleiner |
| 9,439,782 B2 | 9/2016 | Kleiner |
| 2002/0010472 A1 | 1/2002 | Kuslich et al. |
| 2002/0049448 A1 | 4/2002 | Sand et al. |
| 2002/0058947 A1 | 5/2002 | Hochschuler et al. |
| 2002/0099377 A1 | 7/2002 | Zucherman et al. |
| 2002/0116006 A1 | 8/2002 | Cohen |
| 2003/0009169 A1 | 1/2003 | Young et al. |
| 2003/0083748 A1 | 5/2003 | Lee et al. |
| 2003/0125739 A1 | 7/2003 | Bagga et al. |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz et al. |
| 2004/0073314 A1 | 4/2004 | White et al. |
| 2004/0087956 A1 | 5/2004 | Weikel et al. |
| 2004/0133211 A1 | 7/2004 | Raskin et al. |
| 2004/0133217 A1 | 7/2004 | Watschke |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0162616 A1 | 8/2004 | Simonton et al. |
| 2004/0167532 A1 | 8/2004 | Olson, Jr. et al. |
| 2004/0176853 A1 | 9/2004 | Sennett et al. |
| 2004/0215201 A1 | 10/2004 | Lieberman |
| 2004/0230211 A1 | 11/2004 | Moutafis et al. |
| 2005/0070900 A1 | 3/2005 | Serhan et al. |
| 2005/0070912 A1 | 3/2005 | Voellmicke |
| 2005/0080443 A1 | 4/2005 | Fallin et al. |
| 2005/0096601 A1 | 5/2005 | Doyle |
| 2005/0112091 A1 | 5/2005 | DiMauro et al. |
| 2005/0118550 A1 | 6/2005 | Turri |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0216002 A1 | 9/2005 | Simonson |
| 2005/0216018 A1 | 9/2005 | Sennett |
| 2005/0251146 A1 | 11/2005 | Martz et al. |
| 2005/0251257 A1 | 11/2005 | Mitchell et al. |
| 2005/0261781 A1 | 11/2005 | Sennett et al. |
| 2005/0278026 A1 | 12/2005 | Gordon et al. |
| 2005/0283150 A1 | 12/2005 | Moutafis et al. |
| 2006/0004367 A1 | 1/2006 | Alamin et al. |
| 2006/0015184 A1 | 1/2006 | Winterbottom et al. |
| 2006/0058585 A1 | 3/2006 | Oberlaender et al. |
| 2006/0058807 A1 | 3/2006 | Landry et al. |
| 2006/0100304 A1 | 5/2006 | Vresilovic et al. |
| 2006/0100705 A1 | 5/2006 | Puno et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0142858 A1 | 6/2006 | Colleran et al. |
| 2006/0154366 A1 | 7/2006 | Brown et al. |
| 2006/0155170 A1 | 7/2006 | Hanson et al. |
| 2006/0167461 A1 | 7/2006 | Hawkins et al. |
| 2006/0190081 A1 | 8/2006 | Kraus |
| 2006/0229550 A1 | 10/2006 | Staid et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0010824 A1 | 1/2007 | Malandain et al. |
| 2007/0043376 A1 | 2/2007 | Leatherbury et al. |
| 2007/0043442 A1 | 2/2007 | Abernathie |
| 2007/0067034 A1 | 3/2007 | Chirico et al. |

(56) References Cited

U.S. PATENT DOCUMENTS

| | | |
|---|---|---|
| 2007/0073110 A1 | 3/2007 | Larson et al. |
| 2007/0073294 A1 | 3/2007 | Chin et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0185496 A1 | 8/2007 | Beckman et al. |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Luo et al. |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0276406 A1 | 11/2007 | Mahoney et al. |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0033440 A1 | 2/2008 | Moskowitz et al. |
| 2008/0058606 A1 | 3/2008 | Miles et al. |
| 2008/0071284 A1 | 3/2008 | Lechmann et al. |
| 2008/0086142 A1 | 4/2008 | Kohm et al. |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0161924 A1 | 7/2008 | Viker |
| 2008/0172127 A1 | 7/2008 | Perez-Cruet et al. |
| 2008/0177294 A1* | 7/2008 | O'Neil .............. A61B 17/1617 606/167 |
| 2008/0195058 A1 | 8/2008 | Moutafis et al. |
| 2008/0195101 A1* | 8/2008 | Lechot .............. A61B 17/1617 606/79 |
| 2008/0228225 A1 | 9/2008 | Trautwein et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0255666 A1 | 10/2008 | Fisher et al. |
| 2008/0260598 A1 | 10/2008 | Gross et al. |
| 2008/0269904 A1 | 10/2008 | Voorhies |
| 2008/0288071 A1 | 11/2008 | Biyani et al. |
| 2008/0300598 A1 | 12/2008 | Barreiro et al. |
| 2009/0043312 A1 | 2/2009 | Koulisis |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1 | 4/2009 | Zhang et al. |
| 2009/0124860 A1 | 5/2009 | Miles et al. |
| 2009/0124980 A1 | 5/2009 | Chen |
| 2009/0125066 A1 | 5/2009 | Krau et al. |
| 2009/0142385 A1 | 6/2009 | Gross et al. |
| 2009/0182429 A1 | 7/2009 | Humphreys et al. |
| 2009/0187194 A1 | 7/2009 | Hamada |
| 2009/0192350 A1 | 7/2009 | Meja |
| 2009/0192403 A1 | 7/2009 | Gharib et al. |
| 2009/0198243 A1 | 8/2009 | Melsheimer |
| 2009/0198245 A1 | 8/2009 | Phan |
| 2009/0198249 A1 | 8/2009 | Ziegler |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0234455 A1 | 9/2009 | Moskowitz et al. |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai et al. |
| 2009/0292361 A1 | 11/2009 | Lopez |
| 2009/0299477 A1 | 12/2009 | Clayton et al. |
| 2009/0306671 A1 | 12/2009 | McCormack et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0021518 A1 | 1/2010 | Scifert et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0114147 A1 | 5/2010 | Biyani |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145452 A1 | 6/2010 | Blaylock et al. |
| 2010/0145461 A1 | 6/2010 | Landry et al. |
| 2010/0152853 A1 | 6/2010 | Kirschman |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191241 A1 | 7/2010 | McCormack et al. |
| 2010/0191334 A1 | 7/2010 | Keller |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |

(56) References Cited

U.S. PATENT DOCUMENTS

| | | |
|---|---|---|
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2010/0331891 A1 | 12/2010 | Culbert et al. |
| 2011/0014587 A1 | 1/2011 | Spagnoli et al. |
| 2011/0015638 A1 | 1/2011 | Pischl et al. |
| 2011/0015748 A1 | 1/2011 | Molz, IV et al. |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0054538 A1 | 3/2011 | Zehavi et al. |
| 2011/0071527 A1* | 3/2011 | Nelson ............... A61B 17/1624 606/85 |
| 2011/0093005 A1 | 4/2011 | Strokosz et al. |
| 2011/0106162 A1 | 5/2011 | Ballard et al. |
| 2011/0144687 A1 | 6/2011 | Kleiner |
| 2011/0160777 A1 | 6/2011 | Spagnoli et al. |
| 2011/0184412 A1 | 7/2011 | Scifert et al. |
| 2011/0208226 A1 | 8/2011 | Fatone et al. |
| 2011/0213372 A1* | 9/2011 | Keefer ............... A61B 17/1659 606/85 |
| 2011/0230970 A1 | 9/2011 | Lynn et al. |
| 2011/0257478 A1 | 10/2011 | Kleiner et al. |
| 2012/0022603 A1 | 1/2012 | Kirschman |
| 2012/0022651 A1 | 1/2012 | Akyuz et al. |
| 2012/0029635 A1 | 2/2012 | Schoenhoeffer et al. |
| 2012/0035668 A1 | 2/2012 | Manninen et al. |
| 2012/0035729 A1 | 2/2012 | Glerum et al. |
| 2012/0065613 A1 | 3/2012 | Pepper et al. |
| 2012/0065687 A1 | 3/2012 | Ballard et al. |
| 2012/0071981 A1 | 3/2012 | Farley et al. |
| 2012/0078315 A1 | 3/2012 | Sweeney |
| 2012/0089185 A1 | 4/2012 | Gabelberger |
| 2012/0123546 A1 | 5/2012 | Medina |
| 2012/0158146 A1 | 6/2012 | Glerum et al. |
| 2012/0197311 A1 | 8/2012 | Kirschman |
| 2012/0215316 A1 | 8/2012 | Mohr et al. |
| 2012/0259335 A1 | 10/2012 | Scifert et al. |
| 2013/0006364 A1 | 1/2013 | McCormack et al. |
| 2013/0006365 A1 | 1/2013 | Pepper et al. |
| 2013/0006366 A1 | 1/2013 | Farley et al. |
| 2013/0073041 A1 | 3/2013 | Scifert et al. |
| 2013/0110169 A1 | 5/2013 | Hynes et al. |
| 2013/0158664 A1 | 6/2013 | Palmatier et al. |
| 2013/0178940 A1 | 7/2013 | Farley |
| 2014/0012383 A1 | 1/2014 | Triplett et al. |
| 2014/0100657 A1 | 4/2014 | McCormack et al. |
| 2014/0156006 A1 | 6/2014 | Bannigan et al. |
| 2014/0172103 A1 | 6/2014 | O'Neil et al. |
| 2014/0172106 A1 | 6/2014 | To et al. |
| 2014/0207239 A1 | 7/2014 | Barreiro |
| 2014/0228955 A1 | 8/2014 | Weiman |
| 2014/0236296 A1 | 8/2014 | Wagner et al. |
| 2014/0236297 A1 | 8/2014 | Iott et al. |
| 2014/0236298 A1 | 8/2014 | Pinto |
| 2014/0257405 A1 | 9/2014 | Zappacosta et al. |
| 2014/0257490 A1 | 9/2014 | Himmelberger et al. |
| 2014/0276896 A1 | 9/2014 | Harper |
| 2014/0277497 A1 | 9/2014 | Bennett et al. |
| 2014/0287055 A1 | 9/2014 | Kunjachan |
| 2014/0288652 A1 | 9/2014 | Boehm et al. |
| 2014/0296985 A1 | 10/2014 | Balasubramanian et al. |
| 2014/0303675 A1 | 10/2014 | Mishra |
| 2014/0303731 A1 | 10/2014 | Glerum |
| 2014/0303732 A1 | 10/2014 | Rhoda et al. |
| 2014/0309268 A1 | 10/2014 | Arnou |
| 2014/0309548 A1 | 10/2014 | Merz et al. |
| 2014/0309697 A1 | 10/2014 | Iott et al. |
| 2014/0309714 A1 | 10/2014 | Mercanzini et al. |
| 2016/0106551 A1 | 4/2016 | Grimberg et al. |

FOREIGN PATENT DOCUMENTS

| | | |
|---|---|---|
| JP | 2002-052331 | 2/2002 |
| JP | 2009-534140 | 9/2009 |
| JP | 2009-535115 | 10/2009 |
| WO | WO 95/22402 | 8/1995 |
| WO | WO 99/08627 | 2/1999 |
| WO | WO 02/17801 | 3/2002 |
| WO | WO 2005/037149 | 4/2005 |
| WO | WO 2005/071190 | 8/2005 |
| WO | WO 2007/122006 | 11/2007 |
| WO | WO 2007/127666 | 11/2007 |
| WO | WO 2012/031267 | 3/2012 |

OTHER PUBLICATIONS

U.S. Appl. No. 29/542,927, filed Oct. 19, 2015, Kleiner.
U.S. Appl. No. 15/220,795, filed Jul. 27, 2016, Kleiner.
U.S. Appl. No. 15/261,287, filed Sep. 9, 2016, Kleiner.
"BAK® /Proximity™ (BP®) Cage", Zimmer Website, as early as Oct. 23, 2007, available at www.zimmer.com/z/ctl/op/global/action/1/id/7930/template/MP/prcat/M6/prod/y, printed on Jun. 8, 2009, 1 page.
"BAK® Vista® Radiolucent Interbody Fusion System", Zimmer Website, as early as Oct. 25, 2005, available at www.zimmerindia.com/z/ctl/op/global/action/1/id/7809/template/MP/prcat/M6/prod/y, printed on Jun. 8, 2009, pp. 1-2.
"Facet Joint Syndrome," The Cleveland Clinical Foundation, copyright 1995-2008, printed Nov. 19, 2008, available at www.my.clevelandclinc.org/disorders/facet_joint_syndrome/hic_facet_joint_syndrome.aspx, 2 pages.
"Screws, Cages or Both", Spine Universe Website, as early as Aug. 18, 2002, available at www.spineuniverse.com/displayarticle.php/article1363.html, printed on Jun. 8, 2009, pp. 1-13.
"University of Maryland Spine Program: A Patient's Guide to Anterior Lumbar Interbody Fusion with Intervertebral Cages", University of Maryland Medical Center website, as early as 2003, available at www.umm.edu/spinecenter/education/anterior_lumbar_interbody_fusion_with_intervertebral_cages.htm, printed on Jun. 8, 2009, pp. 1-4.
"Vertebral column," from Wikipedia, the free encyclopedia, printed May 19, 2009, retrieved from www.en.wikipedia.org/wiki/Vertebral_column, 6 pages.
"Zygapophysial joint," from Wikipedia, the free encyclopedia, printed May 19, 2009, retrieved from www.en.wikipedia.org/wiki/Zygapophysial_joint, 2 pages.
Ehrenberg, "The 3-D Printing Revolution," Science News, Mar. 9, 2013, pp. 20-25.
Newton, "EOS Teams with Medical Implant Designer to Advance 3D Printing in Medicine," Graphic Speak, 2012, 2 pages.
Ray, "Facet Joint Disorders and Back Pain," published on Spine-Health, Dec. 10, 2002, available at www.spine-health.com/conditions/arthritis/facet-joint-disorders-and-back-pain, 1 page.
Staehler, "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.
Staehler, "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.
Ullrich, "Anterior Cervical Spinal Fusion Surgery," published on Spine-Health, Oct. 7, 2005, available at www.spine-health.com/treatment/back-surgery/anterior-cervical-spinal-fusion-surgery, 2 pages.
Ullrich, "Cervical Spinal Instrumentation," published on Spine-Health, Oct. 7, 2005, available at www.spine-health.com/treatment/back-surgery/cervical-spinal-instrumentation, 2 pages.
Wascher, "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.

(56) References Cited

OTHER PUBLICATIONS

International Search Report for International (PCT) Patent Application No. PCT/US2009/033488, dated Mar. 25, 2009, 2 pages.
Written Opinion for International (PCT) Patent Application No. PCT/US2009/033488, dated Mar. 25, 2009, 9 pages.
Official Action for U.S. Appl. No. 12/367,487, dated Aug. 3, 2011 10 pages.
Notice of Allowance for U.S. Appl. No. 13/277,272, dated Jun. 11, 2012 8 pages.
Official Action for U.S. Appl. No. 13/473,366, dated Jul. 18, 2012 8 pages.
Notice of Allowance for U.S. Appl. No. 13/473,366, dated Sep. 4, 2012, 5 pages.
Official Action for U.S. Appl. No. 13/632,956 dated Mar. 29, 2013, 9 pages.
Official Action for U.S. Appl. No. 13/632,956 dated Aug. 1, 2013, 12 pages.
Official Action for U.S. Appl. No. 13/632,956 dated Dec. 24, 2013, 11 pages.
Notice of Allowance for U.S. Appl. No. 14/461,682 dated May 4, 2016, 6 pages.
Notice of Allowance for U.S. Appl. No. 29/393,737, dated Jan. 11, 2012 9 pages.
Notice of Allowance for U.S. Appl. No. 29/415,847, dated Jul. 17, 2012 10 pages.
Notice of Allowance for U.S. Appl. No. 29/433,403, dated Aug. 7, 2013 9 pages.
Official Action for U.S. Appl. No. 14/887,598, dated Jul. 15, 2016 8 pages.
Official Action for U.S. Appl. No. 13/168,611 dated Apr. 15, 2013, 7 pages.
Official Action for U.S. Appl. No. 13/168,611 dated Aug. 15, 2013, 12 pages.
Official Action for U.S. Appl. No. 13/168,611 dated May 23, 2014, 10 pages.
Final Action for U.S. Appl. No. 13/168,611 dated Oct. 6, 2014, 10 pages.
Official Action for U.S. Appl. No. 13/168,611 dated Apr. 13, 2015, 11 pages.
Final Action for U.S. Appl. No. 13/168,611 dated Jun. 25, 2015, 9 pages.
Official Action for U.S. Appl. No. 13/168,611 dated Sep. 8, 2015, 4 pages.
Notice of Allowance for U.S. Appl. No. 13/168,611 dated Sep. 28, 2015, 12 pages.

* cited by examiner

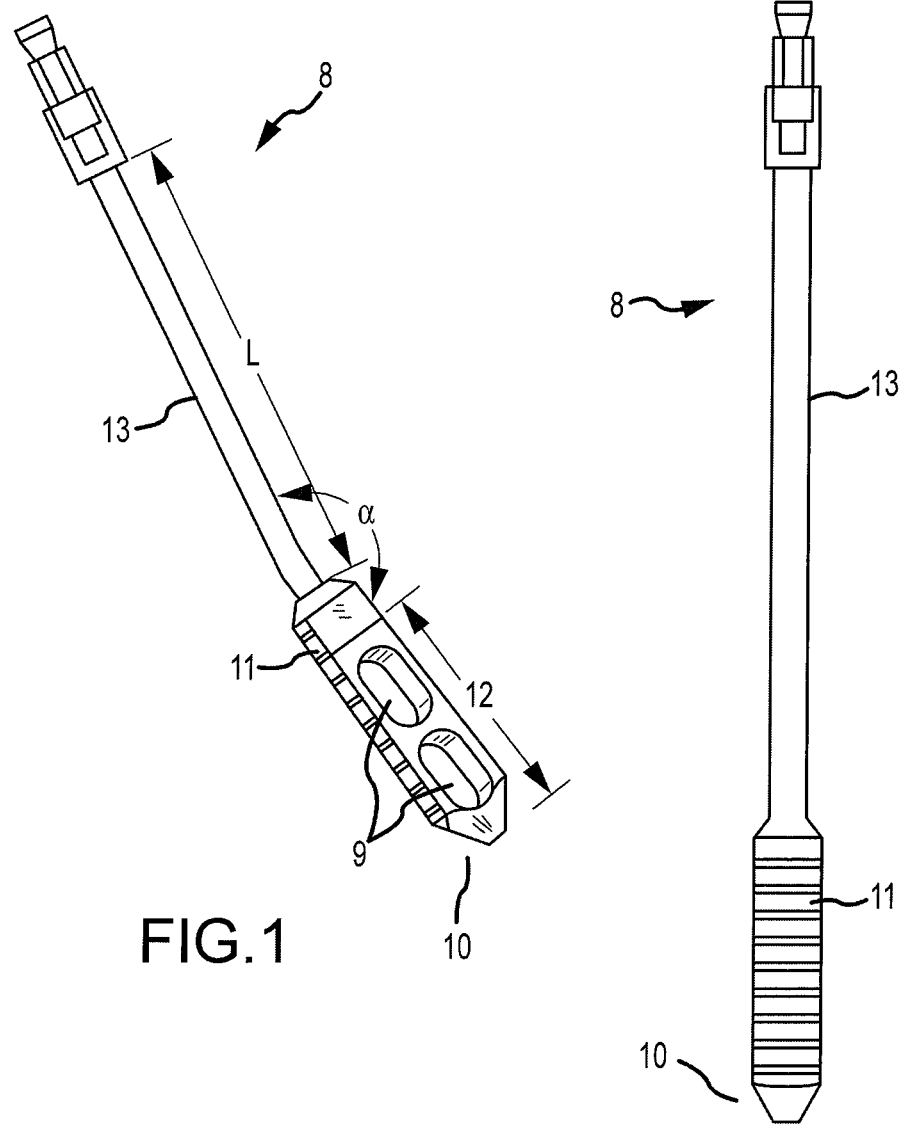

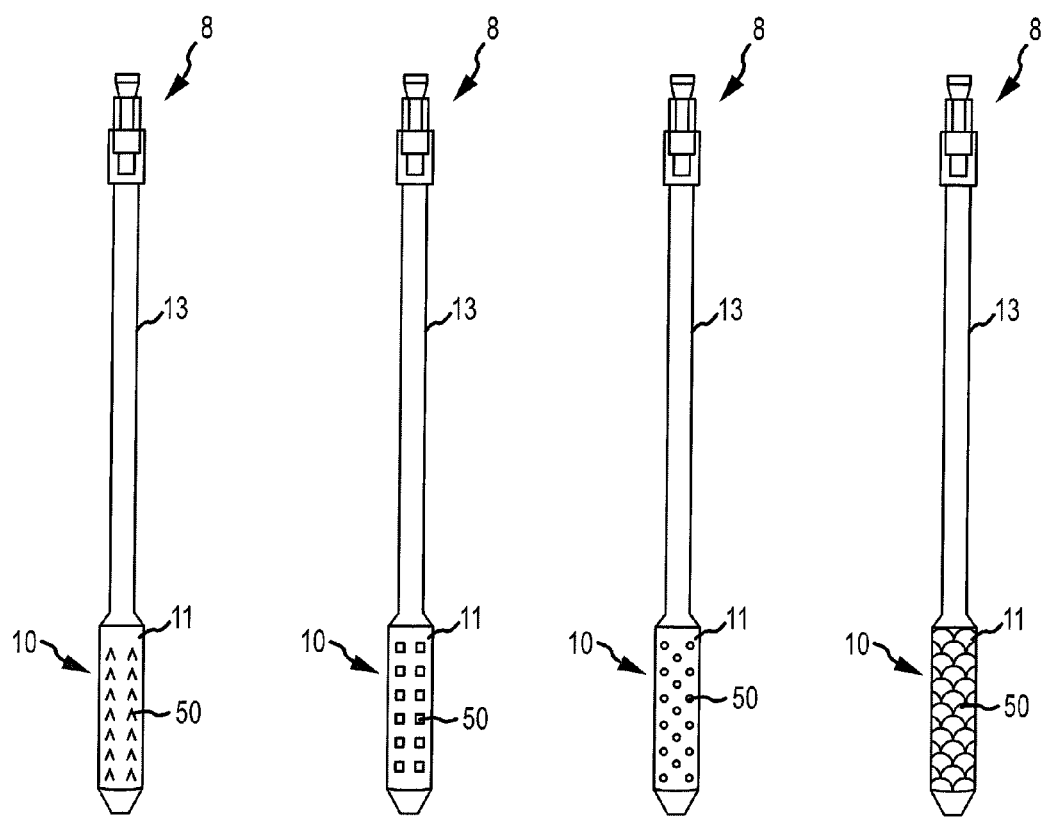

DEVICES AND METHODS FOR PREPARING AN INTERVERTEBRAL WORKSPACE

RELATED APPLICATIONS

The present application is a continuation of U.S. patent application Ser. No. 13/168,611, filed Jun. 24, 2011 (now U.S. Pat. No. 9,247,943, issued Feb. 2, 2016), which is a continuation-in-part patent application which claims the benefit of priority from commonly owned and co-pending U.S. patent application Ser. No. 12/367,487, filed Feb. 6, 2009 (now U.S. Pat. No. 8,088,163, issued Jan. 3, 2012), and U.S. Provisional Patent Application No. 61/358,149, filed Jun 24, 2010, the entire disclosures of which are hereby expressly incorporated by reference in this disclosure as if set forth fully herein.

FIELD OF THE INVENTION

The present disclosure relates to the field of medical devices and is generally directed toward tools and methods for distracting or otherwise preparing an intervertebral disc space for various procedures to be performed within the disc space.

BACKGROUND OF THE INVENTION

This invention relates to devices and methods for preparing and cleaning an intervertebral workspace. More specifically, the present invention relates to tools and methods for intervertebral distraction and cleaning of an intervertebral space including, for example, spinal end plates.

Spondylosyndesis, or spinal fusion, is a surgical technique used to combine two or more vertebrae into a single, rigid working unit. This is typically achieved by introducing a supplementary bone tissue, such as an autograft or allograft, into the intervertebral space between two target vertebrae, at the location that is typically occupied by an intervertebral disc. The supplementary bone tissue is then used in conjunction with the patient's natural osteoblastic processes in order to grow bone or osseous tissue between the two or more target vertebrae, which acts to fuse them together into the desired rigid unit. This procedure is used primarily to eliminate pain that is caused by abnormal motion of one or both of the target vertebrae; pain relief occurs by immobilizing the vertebrae themselves and preventing the abnormal motion.

Alternatively, surgically implantable synthetic intervertebral fusion cages or devices may be used to perform spinal fusion procedures.

Surgically implantable intervertebral fusion cages are well known in the art and have been actively used to perform spinal fusion procedures for many years. Their use became popularized during the mid 1990's with the introduction of the BAK Device from Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone growth onto or through an implant that is placed between the vertebrae. An implant or insert may or may not promote fusion of the adjacent vertebral bodies, may be an artificial spinal disc, may permit surface ingrowth, and may be made of bone or inert material, such as titanium.

Current methods of forming and preparing a disc space between vertebrae are known to include various grasping instruments, drills, rotating buns, chisels, and other scraping implements. There has been a long felt and unmet need to provide a distraction tool which is capable of spreading or separating vertebral bodies and further capable of cleaning, scouring, and/or removing tissue from a disc space.

BRIEF SUMMARY OF THE INVENTION

Embodiments of the present invention disclose various surgical tools such as distractors which comprise features adapted to remove unwanted tissue, debris, and/or contamination from an intervertebral disc space. In one embodiment, a distractor tool is provided which comprises a unique configuration on its head or distal end which generally facilitates insertion of the tool into a disc space and further enables the removal of tissue and undesired substances from the disc space and the spinal end plates. In various embodiments, this is accomplished by providing a surgical tool with a distal end having a unique geometry such that insertion of the tool is generally unobstructed while extraction of the tool generally enables the scraping and/or frictional removal of debris which may be present within a workspace.

In various embodiments, a plurality of surgical tools is provided wherein the plurality of surgical tools comprises tools of different sizes and/or shapes. Thus, a user or surgeon is provided with numerous different shaft and distal end combinations so that the appropriate tool may be selected for the appropriate application. One of skill in the art will recognize that different patient characteristics and operating conditions may dictate different device selection. Accordingly, the present invention contemplates providing a plurality of tools which offers such discretion.

Other embodiments of the present invention provide a means for a user to selectively activate or actuate features of an intervertebral workspace tool in order to scrape or otherwise collect various tissue disposed within the disc space. For example, it is contemplated that tools of the present invention comprise movable features, such as selectively engageable clam shell or shovel-type devices which are activated and/or controlled by features at a proximal end of the device adapted for user interaction. In alternative embodiments, user operated features are provided such as pressure applying means. Pressure applying means of the present invention may comprise, for example, a working shaft and distal end to which a vacuum pressure is supplied, thereby drawing debris toward at least a distal end of the tool(s).

In various embodiments, one or more distraction tools are provided, the one or more distraction tools being capable of transmitting or applying a positive pressure to a disc space. For example, a quantity of fluid or gas may be directed through portions of a distraction tool by a positive pressure for impacting various regions and materials within the disc space.

In further embodiments, the present invention comprises various fenestrations, portals, and/or apertures adapted for transmitting a pressure (e.g. a positive or negative pressure) induced by a device located external to the workspace and transmitted through portions of a tool. Vacuum pressures may be selectively applied to various portions of an intervertebral work space tool based on necessity and/or user preference.

Various embodiments of the present invention provide for detachable and/or disposable shafts which connect to disc space tool heads and/or distal ends. For example, novel intervertebral disc space tool heads of the present invention, as shown and described herein, may be detachably disposed on an elongated shaft. In various embodiments, elongated shafts of the present invention may comprise various surgical grade materials, such as surgical steel, titanium, and other suitable materials. The shafts may be reusable for at least two or more procedures and may be generally adapted for autoclaving and other required and/or appropriate sanitation methods. In alternative embodiments, elongated shafts of the present invention are comprised of a material which generally enables the shafts to be disposable. For example, disposable shafts may be comprised of a material which is not suited for sanitization and repeated use and/or material which renders disposal of the shaft economically practical.

In various embodiments, disposable shafts are provided which are adapted to be connected to detachable distal portions, heads, or working portions. For example, disposable shafts may be provided where the shafts are capable of being securely anchored to a head portion so as to minimize or eliminate the risk of detachment and subsequent depositing of a distractor head assembly within an intervertebral workspace. In one embodiment, shafts of the present invention are detachably anchored to a head portion through the use of male/female threaded portions disposed on opposite devices. Detachable shafts of the present invention allow for the ability to selectively apply an appropriate shaft to a desired head or distal portion of a tool. For example, detachable shafts of the present invention allow for the ability to utilize different size, length, and shaped shafts on patients of different sizes and dimensions while utilizing a similarly appropriate distal end tool or distractor wedge. In this manner, the need to store or keep on hand numerous or excessive amounts of tools is reduced. Likewise, manufacturing costs of producing a similarly excessive amount of tools is reduced.

In various embodiments, tools of the present invention are made from a biocompatible material such as a thermal plastic (e.g. PEEK), a polymer, metal, combination thereof or otherwise, such as desired and/or is appropriate.

In various embodiments, one or more portions of tools of the present invention comprise rasps, teeth, or structures having various combinations of plateaus and/or valleys for contact with a vertebral body, end plate, and various material and features located within a vertebral body. The plurality of rasps, teeth, or scales are configured to facilitate insertion of the device into the intervertebral work space while not substantially preventing or impeding removal of the device. In embodiments, the teeth or geometry of portions of the tools are adapted to facilitate the removal of at least the outer most cell layers of bone to gain access to vascular bone tissue within the disc space and otherwise clean or clear the work space. For example, various features shown and described in U.S. Pat. No. 7,461,803 to Boerner and U.S. Pat. No. 7,632,276 to Fishbein, which are incorporated by reference herein in their entireties, and variations thereof, may be incorporated into embodiments of the present invention. In one embodiment, a distal end or head of a distraction tool comprises a generally hollow feature wherein peripheral outer surfaces are capable of dislodging, scraping, and/or cutting various materials and directing the materials to an interior hollow portion so that the materials may be removed from the disc space along with the distraction tool.

In various embodiments, the present invention comprises channels or flutes for guiding materials that have been dislodged or scraped away from portions of the intervertebral workspace. For example, a distal end of a spinal distractor tool according to embodiments of the present invention may comprise channels or apertures which direct material that has been scraped by additional features of the tool into a region or volume of the distractor that is adapted for securing and/or temporarily retaining the dislodged material. In further embodiments, additional features are employed to compliment such channels or retaining apertures. For example, in one embodiment, a vacuum pressure is applied through a shaft portion of a distractor tool which facilitates maintaining debris and/or dislodged materials within receiving apertures of the present invention while the device is manipulated or removed from the intervertebral workspace.

In various embodiments, the present invention comprises features and devices for physically sealing, closing, or otherwise containing receiving apertures. For example, receiving apertures or fenestrations which are generally open during distraction procedures may be selectively sealed or closed by a user through the use of features disposed at a proximal end of the device.

The present invention further contemplates a method including the step of distracting the disc space between adjacent vertebral bodies, and in particular, the distracting step may include the step of inserting a distractor having a disc penetrating extension into a disc space between adjacent vertebral bodies and against end plates of the adjacent vertebral bodies. The depth of penetration of the distractor into the disc space is preferably controlled. The method may further include the step of changing disc penetrating extensions of the distractor in accordance with a desired distractor distance between adjacent vertebral bodies.

Incorporated by reference in their entireties are the following U.S. patents and patent applications directed generally to methods and apparatus related to spinal procedures, thus providing written description support for various aspects of the present disclosure. The U.S. patents and pending applications incorporated by reference are as follows: U.S. Pat. Nos. 7,406,775 to Funk, et al.; 7,387,643 to Michelson; 7,341,590 to Ferree; 7,288,093 to Michelson; 7,207,992 to Ritland; 7,077,864 Byrd III, et al.; 7,025,769 to Ferree; 6,719,795 to Cornwall, et al.; 6,364,880 to Michelson; 6,328,738 to Suddaby; 6,290,724 to Marino; 6,113,602 to Sand; 6,030,401 to Marino; 5,865,846 to Bryan, et al.; 5,569,246 to Ojima, et al.; 5,527,312 to Ray; and 2008/0255564 to Michelson.

A variety of known vacuum pumps and devices may be utilized in combination with aspects of the present invention. By way of example, U.S. Pat. Nos. 5,282,744 to Meyer, 4,580,978 to Motola et al., 4,991,570 to Bullard, 5,311,640 to Holland, and U.S. Patent Application Publication No. 2007/0172790 to Doucette, Jr. et al., which are incorporated by reference in their entireties herein, generally relate to the field of dentistry. Various features and aspects described in these references may be incorporated into aspects of the present invention.

In various embodiments, a positive pneumatic pressure may be applied to a disc space through portions of a tool 8. For example, air or other gases and/or fluids may be provided to a disc space to blast or clear a surgical work area or disc space. U.S. Pat. Nos. 6,004,191 to Schur et al., 4,430,062 to Henrichsen et al., 4,877,399, 6,216,573 to Moutafis et al., 7,122,017 to Moutafis et al., 6,960,182 to Moutafis et al., 5,944,686 to Patterson et al., and U.S. Patent Application Publication No. 2005/0267443 to Staid et al., which are incorporated by reference herein in their entireties relate to various devices and methods for delivering a volume of air or fluid to a desired location. In various embodiments, the present invention comprises delivering force or pressurized air, gas, fluids, and various combinations thereof to a disc space and a distal end of a distraction tool. For example, ambient air, inert gases, oxygen, water, saline, and various combinations thereof may be directed to a disc space through features of the present invention (e.g. channels housed within a distractor). One of skill in the art will recognize that such features may direct such substances to a portion of a disc space (e.g. a disc end plate) and/or to a portion of the tool 8 which has become contaminated with various fluid, tissue, debris etc. (e.g. a distal end).

In various embodiments, an elongate shaft is comprised of one or more flexible materials, thus creating a shaft which is resiliently deformable. For example, shafts of the present invention may comprise helical spring members designed to yield a certain amount under appropriate moments forces yet generally restore themselves to a linear elongate arrangement absent a certain magnitude of force. Alternatively, a shaft may be comprised of elastically deformable plastics allowing for flexible movement away from its axis under external force and return to or approximately to an initial position in the absence of such a force. Thus, embodiments of the present invention contemplate an elongate shaft adapted for receiving and transmitting a compressive force applied by a surgeon, yet provides enough compliance in moment to accommodate various obstructions and prevent or reduce the risk of devices becoming "wedged" or lodged into a disc space. In various embodiments, various polyethylenes, polyvinylchloride, urethanes, PEEK, elastically deformable metals, and other similar materials may comprise flexible elongate shafts of the present invention. In one embodiment, a flexible shaft comprises a biocompatible material (e.g. PEEK). However, as one of ordinary skill in the art will recognize, the shaft is not an implantable device. Thus, in alternative embodiments, the shaft is comprised various surgical grade materials suitable for surgical tools generally.

In various embodiments, the present invention comprises various imaging devices for providing feedback to a user.

BRIEF DESCRIPTION OF THE FIGURES

FIG. 1 is a front perspective view of one embodiment of a distraction tool;

FIG. 2 is a side elevation view of one embodiment of a distraction tool;

FIGS. 11a-11d are elevation views of various embodiments of the present invention.

Figure 3:
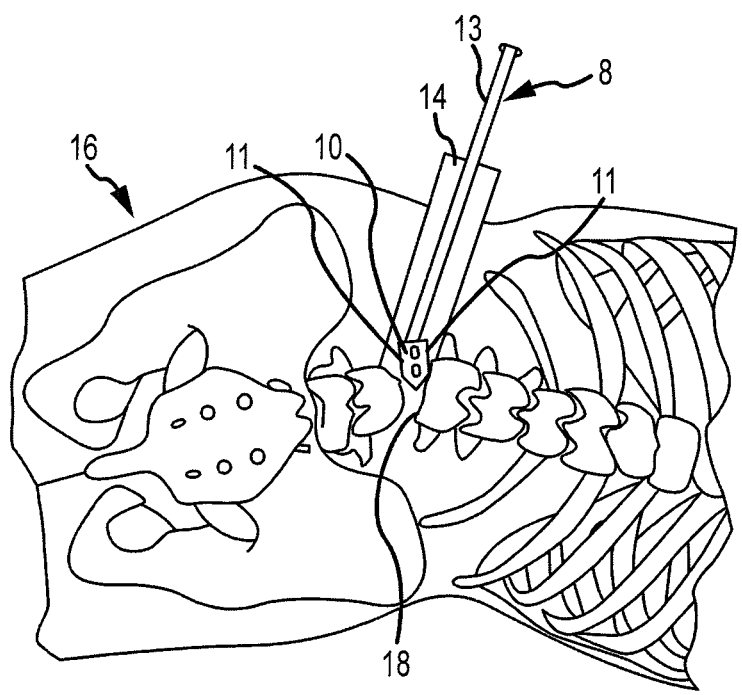
FIG. 3 is an elevation view of one embodiment of a distraction tool of the present invention in use.

It should be understood that the drawings are not necessarily to scale. In certain instances, details that are not necessary for an understanding of the invention or that render other details difficult to perceive may have been omitted from these drawings. It should be understood, of course, that the invention is not limited to the particular embodiments illustrated in the drawings.

DETAILED DESCRIPTION

In accordance with embodiments of the present disclosure, a distraction tool 8 is provided, the distraction tool 8 having an elongated handle of a predetermined length L. The handle is substantially cylindrical in shape and comprises a head 10 at a distal end configured to generate an opening in tissue, the head portion 10 being offset from the handle portion by an angle α such that the head and the handle are not located in the same plane. Referring specifically to FIGS. 1 and 2, the head distraction spacer 10 is configured at an angle between approximately 1 and 45 degrees with respect to a longitudinal axis of the shaft 13 so that it may enter a disk space when an operating cannula is not at a right angle to the disk space. In a preferred embodiment, the head 10 is configured at angle between approximately 3 and 25 degrees with respect to a longitudinal axis of the shaft 13. For purposes of illustration, and without wishing to be held to any one embodiment, the following U.S. Patents are incorporated herein by this reference in order to provide an illustrative and enabling disclosure and general description of a distraction tool without a head portion being offset from the handle portion by an angle: U.S. Pat. Nos. 5,836,948 to Zucherman et al.; 5,860,977 to Zucherman et al.; 5,944,658 to Koros et al.; 6,238,397 to Zucherman et al.; 6,224,599 to Baynham et al.; 6,261,296 to Aebi et al.; and U.S. Design Patent No. D374283 to Michelson. Each of the foregoing discloses a distractor or distraction tool having a head portion that is in the same plane as the handle portion and, for the sake of simplicity, will be collectively referred to herein as having a head portion and a handle portion.

The handle of the distraction tool 8 is generally cylindrical in shape and has a length L ranging from about 140 cm to about 170 cm, and preferably from about 160 cm to about 165 cm, and has a diameter ranging from about 4 mm to about 5 mm The distal end of the handle may optionally include features for attachment to other surgical instruments, though this is not necessary for purposes of the present invention. The proximal, or head, end of the distraction tool comprises a head portion 10 having a length ranging from about 15 mm to about 50 mm, a width ranging from about 40 mm to about 55 mm, and a height or thickness ranging from about 6 mm to about 16 mm. Thus, in some embodiments, the head portion is generally rectangular in shape. The head portion includes a distal tip located at the distal terminus of the head portion. In some embodiments, the distal tip is pointed such that the height or thickness of the head portion and/or the width of the head portion is gradually reduced from the head portion to the distal tip, culminating in a pointed edge. The pointed edge is the initial portion of the distraction tool to make contact with the target tissue, and thus facilitates dissection of the target tissue by displacing the tissue as it is moved forward into the tissue. The pointed tip thus makes it easier for the user to move the distraction tool into the target tissue. The head portion 10 of the distraction tool is offset from the handle portion by an angle ranging from approximately 5 to 45 degrees, and preferably from about 15 to 25 degrees.

In some embodiments and referring now to FIG. 1, the head portion 10 of the distraction tool 8 includes at least one recess or fenestration 9 located on a face of the head 10. In various embodiments, the at least one recess or fenestration 9 is present only on a single side of the distraction tool and does not pass through the entire head portion of the distraction tool. In alternative embodiments, the at least one recess 9 comprises a through hole disposed within the head 10 of the tool 8. The at least one recess or fenestration may be of any size or shape and the present disclosure is intended to include recesses and/or fenestrations of any size and shape that are capable of fitting on the head portion of the distraction tool. In some embodiments, the at least one recess or fenestration 9 is generally square or rectangular in shape. The at least one recess or fenestration may be used in conjunction with x-rays or similar forms of radiation to view the distraction tool during use and determine whether it has been properly positioned in the surgical site. In various embodiments, the at least one recess or fenestration 9 may be adapted to collect, trap, and/or secure tissue, material, and debris. In various embodiments, a vacuum pressure is applied to the at least one fenestration 9 to further enable or facilitate removal of fluids and materials from a disc space.

FIG. 2 is a side elevation view of one embodiment of a distraction tool 8. In various embodiments, at least a portion of the head 10 of the distraction tool 8 comprises a textured surface 11. The textured surface 11 may comprise rasps, teeth, or scales adapted for removing debris, tissue, and material from a surface and/or work space. Rasps, teeth, or scales of the present invention are adapted to facilitate the insertion of the tool 8 into a workspace. Removal of the tool 8 from a workspace is not unduly restricted by one or more textured surfaces 11. However, one or more textured surfaces 11 are adapted to scrape and/or remove various unwanted tissue and debris disposed within an intervertebral workspace, such as from an end plate. Thus, the preparation of a disc space for insertion of an intervertebral cage or other devices/procedures is facilitated and the need for additional tools (e.g. scrapers) is reduced or eliminated. Tools such as those disclosed in U.S. Pat. No. 7,722,613 to Sutterlin et al., which is hereby incorporated by reference in its entirety, generally comprise additional tools separate and apart from distracters for cleaning a workspace. Tools described in U.S. Pat. No. 7,722,613 to Sutterlin et al., are obviated or rendered less critical by features of the present invention.

FIG. 3 is a front elevation view of one embodiment of a distraction tool of the present invention in use. As shown, a patient 16 is positioned on their side and an operating cannula 14 is utilized to provide access to a work space. A distraction tool 8 according to various embodiments is utilized to prepare an intervertebral workspace. One of ordinary skill in the art will recognize that prior to insertion of an implantable cage and/or other procedures to be performed within the workspace, it is necessary or desirable to remove various tissue and debris from a workspace and a vertebral end plate 18. Accordingly, in various embodiments, the present invention contemplates at least a portion of at least one surface of a distractor tool 8 comprising a textured surface adapted for removing debris and cleaning an intervertebral endplate.

In various embodiments, the at least one surface comprises teeth, rasps, fins, or ridges, which are adapted to allow for insertion, manipulation, and removal of at least a distal end 10 of the device 8 into an intervertebral space while providing the ability to scrape, dislodge, or remove tissue and material. In various embodiments, portions of a device 8 are further capable of retaining, collecting, and/or trapping at least portions of materials dislodged by the tool 8.

Figure 4:
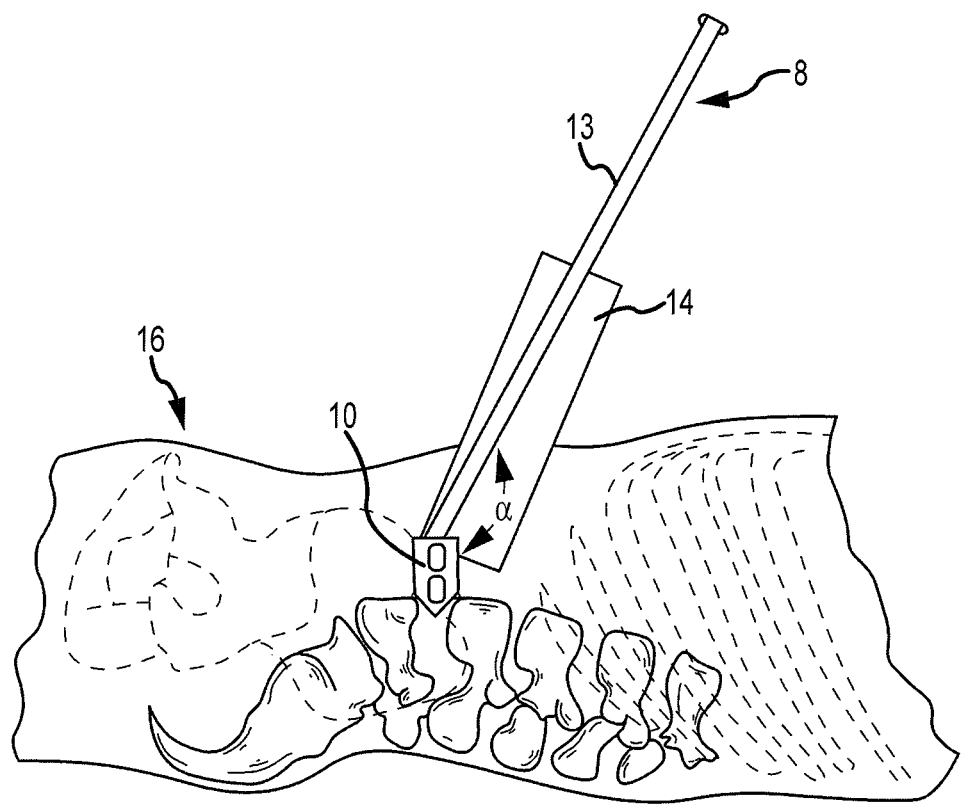
FIG. 4 is an elevation view of one embodiment of a distraction tool of the present invention in use.

FIG. 4 is a side elevation view of a patient 16 positioned on their back and an operating cannula 14 utilized to provide access to a work space. A distraction tool 8 according to various embodiments is utilized to prepare an intervertebral workspace for various procedures. A distal end 10 of a distraction tool 8 is angled at a predetermined angle α with respect to an elongate shaft 13.

In various embodiments, the present invention comprises features and devices for physically sealing, closing, or otherwise containing receiving apertures. For example, receiving apertures or fenestrations which are generally open during distraction procedures may be selectively sealed or closed by a user through the use of features disposed at a proximal end of the device.

In various embodiments, movable features are provided at distal locations of a distraction tool for selectively grasping and/or containing materials dislodged and/or to be removed from a disc space. For example, a distraction wedge 10 may be comprised of two or more portions connected by one or more hinges. Cables or guide wires may be disposed within an elongate shaft 13 of the device 8, the cables or wires extending to a location proximal a user for selective manipulation of the two or more portions. Distal end features of the present invention may comprise disher style scoops or other similar rotatable and/or translatable members for applying a cutting or shearing force to portions of a disc space.

Figure 5:
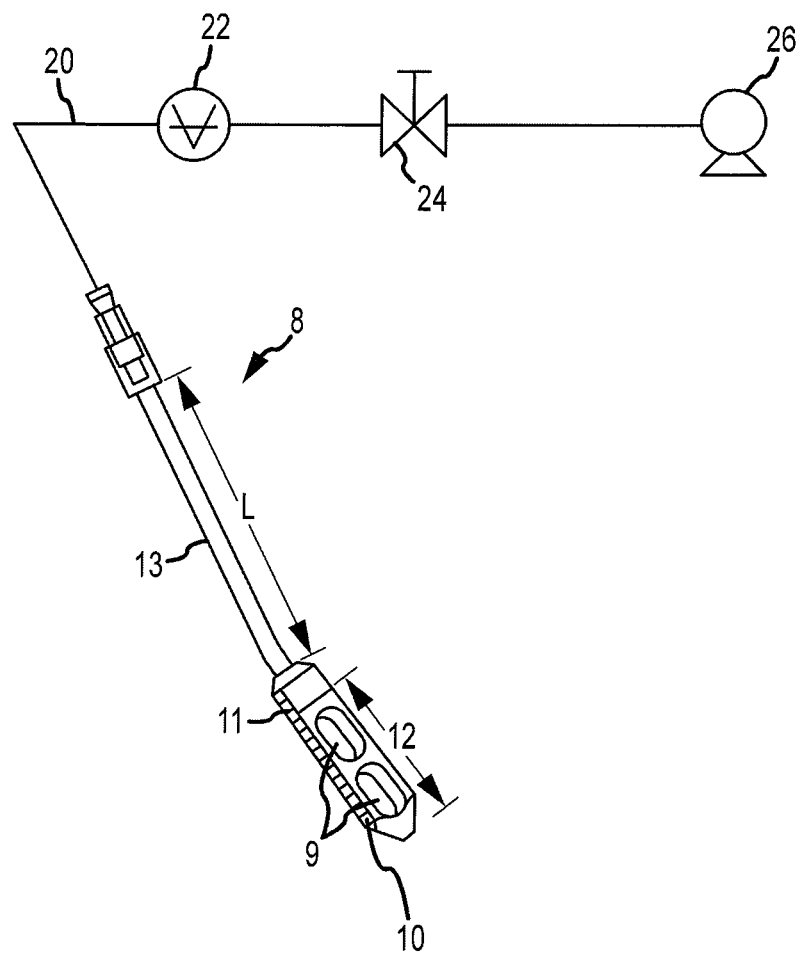
FIG. 5 is a front perspective view of one embodiment of a distraction tool.

FIG. 5 is a front perspective view of one embodiment of a distraction tool 8 comprising vacuum features. As shown, a distraction tool 8 may be connected to a vacuum line 20 adapted to transmit vacuum pressure from a pump 26 to a distal end 10 of the distraction tool 8. In various embodiments, the device may further comprise a hand valve 24 for selectively terminating/applying a vacuum pressure and a pressure gauge 22 for displaying the vacuum pressure applied at a distal end of the device to a user. One of skill in the art will recognize that where a vacuum pump 26 is provided, additional features such as a pressure gauge 22 and valve 24 may, but need not necessarily be provided.

In various embodiments, a pressure may be applied at locations disposed within apertures 9 at a distal end of the tool 8. Thus, for example, tissue and debris dislodged by textured portions 11 of the tool 8 may either be held within apertures 9 or drawn through portions of the tool 8 and removed from a surgical work space and a tool 8. In alternative embodiments, apertures may be provided on exterior portions of a distal end 10 of the tool 8, wherein the apertures are adapted for transmitting vacuum pressure and capturing debris and tissue to be removed from an intervertebral workspace. Distraction tools 8 of the present invention may comprise hollow or partially hollow shafts 13 for transmitting pressure, air, and fluids to or from a surgical workspace/intervertebral space.

One of skill in the art will recognize that, where provided, a hand valve 24 of the present invention may be disposed at a variety of locations with respect to a distraction tool 8. In one embodiment, a user-operated valve 24 is disposed on a portion of the tool 8 (e.g. a proximal end of the tool) such that suction may be initiated without requiring a user to divert significant attention away from the device 8.

A variety of known vacuum pumps and devices may be utilized in combination with aspects of the present invention. By way of example, U.S. Pat. No. 5,282,744 to Meyer, U.S. Pat. Nos. 4,580,978 to Motola et al., 4,991,570 to Bullard, 5,311,640 to Holland, and U.S. Patent Application Publication No. 2007/0172790 to Doucette, Jr. et al., which are incorporated by reference in their entireties herein, generally relate to the field of dentistry. However, various features and aspects described in these references may be incorporated into aspects of the present invention.

In various embodiments, a positive pressure may be applied to a disc space through portions of a tool 8. For example, air or other gases and/or fluids may be provided to a disc space to blast or clear an area to be cleaned. U.S. Pat. Nos. 6,004,191 to Schur et al., 4,430,062 to Henrichsen et al., 4,877,399, which are incorporated by reference herein in their entireties relate to various devices and methods for delivering a volume of air or fluid to a desired location. In various embodiments, the present invention comprises delivering forced or pressurized air, gas, fluids, and various combinations thereof to a disc space and a distal end of a distraction tool 8. For example, ambient air, inert gases, oxygen, water, saline, and various combinations thereof may be directed to a disc space through features of the present invention (e.g. channels housed within a distractor 8). One of skill in the art will recognize that such features may direct such substances to a portion of a disc space (e.g. a disc end plate) and/or to a portion of the tool 8 which has become contaminated with various fluid, tissue, debris, etc. (e.g. a distal end).

One of ordinary skill in the art will appreciate that embodiments of the present disclosure may have various sizes. The sizes of the various elements of embodiments of the present disclosure may be sized based on various factors including, for example, the anatomy of the patient, the person or other device operating the apparatus, the surgical location, physical features of the implant including, for example, width, length and thickness, and the size of other surgical tool(s) being used.

Embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials.

The distraction tools of the present disclosure may be made of any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel.

Figure 6:
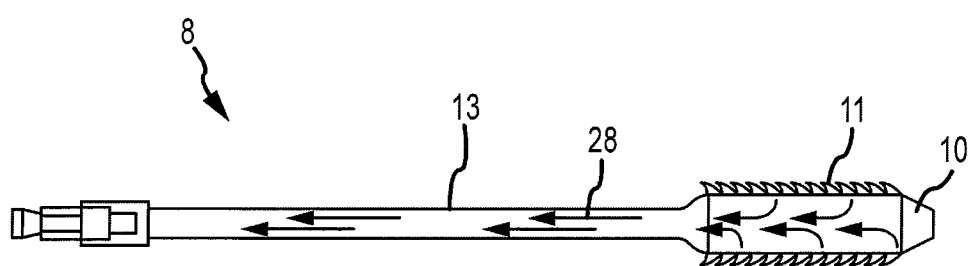
FIG. 6 is a side elevation view of one embodiment of a distraction tool.

FIG. 6 is a side elevation view of a distraction tool according to one embodiment. As shown, a distal end 10 of a distraction tool 8 may comprise textured features 11 adapted to trap, scrape, or otherwise remove tissue, fluids, and debris from an intervertebral workspace. It will be recognized that features of the tool 8 as shown in FIG. 6 are not necessarily to scale. In various embodiments, the textured end 11 is adapted to facilitate insertion of the device 8 into a disc space, capture various debris and materials, and not substantially impede or frustrate removal of the tool 8 from the disc space.

In various embodiments, suction may be applied to a device 8 through a hollow shaft 13 or hollow portion of a shaft. A vacuum pressure may apply a force(s) (indicated by directional arrows 28) capable of withdrawing material from a disc space and/or biasing material that has been dislodged by portions of the tool 8 against or toward a proximal portion of the tool. As used herein, a proximal portion will generally be understood to mean the portion of the tool proximal to a user/surgeon in operation.

Figure 7:
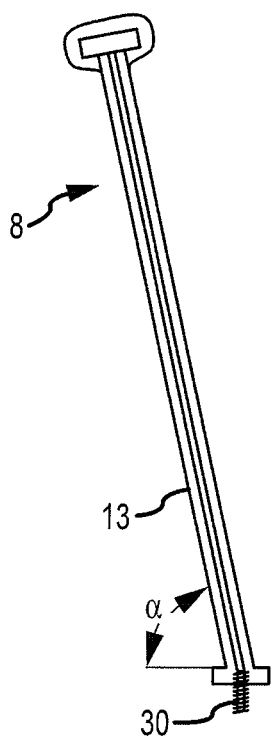
FIG. 7 is a front elevation view of one embodiment of a distraction tool shaft.
Figure 8:
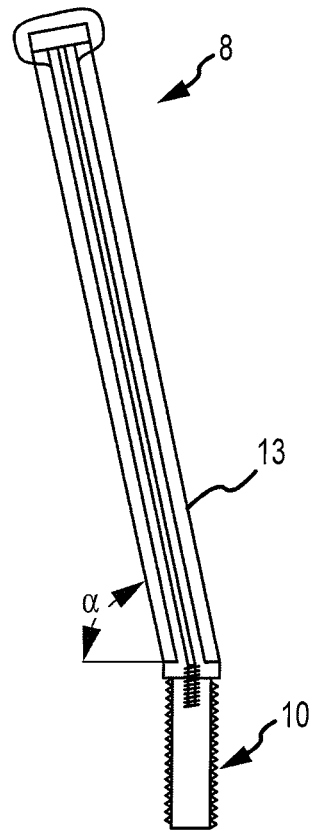
FIG. 8 is a front elevation view of one embodiment of a distraction tool assembly.

In accordance with at least some aspects of at least one embodiment of the present disclosure and referring now to FIGS. 7-8, a distractor tool with a detachable head is provided, the tool 8 having an elongated, hollow handle that is substantially cylindrical in shape. In various embodiments, a distractor tool 8 is provided wherein a head or distal portion 10 is selectively removable from a shaft portion 13. Head portions 10 may be detachably secured to a remainder of the tool 8 by any number of known devices, including, for example, a threaded member 30 for receiving a head 10.

In various embodiments, one or more of the head 10 and handle 13 portions of a distractor tool 8 are disposable. For example, either the head 10, handle 13, or both are comprised of a material which renders the portion(s) suitable for disposable after one or more procedures and/or uses. In various embodiments, a head portion 10 is provided with rivets, scales, ridges, and/or teeth adapted for removing and/or dislodging intervertebral materials. In various embodiments, such features complicate cleaning of the device. Accordingly, various embodiments contemplate the use of a disposable distractor tool head 10 and thereby substantially reduce, for example, risks associated with cross-contamination between patients and devices. In alternative embodiments, one or more textured portions of a distraction tool 8 comprises a geometry which is adapted to be cleaned by standard cleaning and sterilization procedures. Thus, in certain embodiments, distal ends of distraction tools may be cleaned and/or sterilized without the need for disposal or specialized cleaning procedures.

Figure 9:
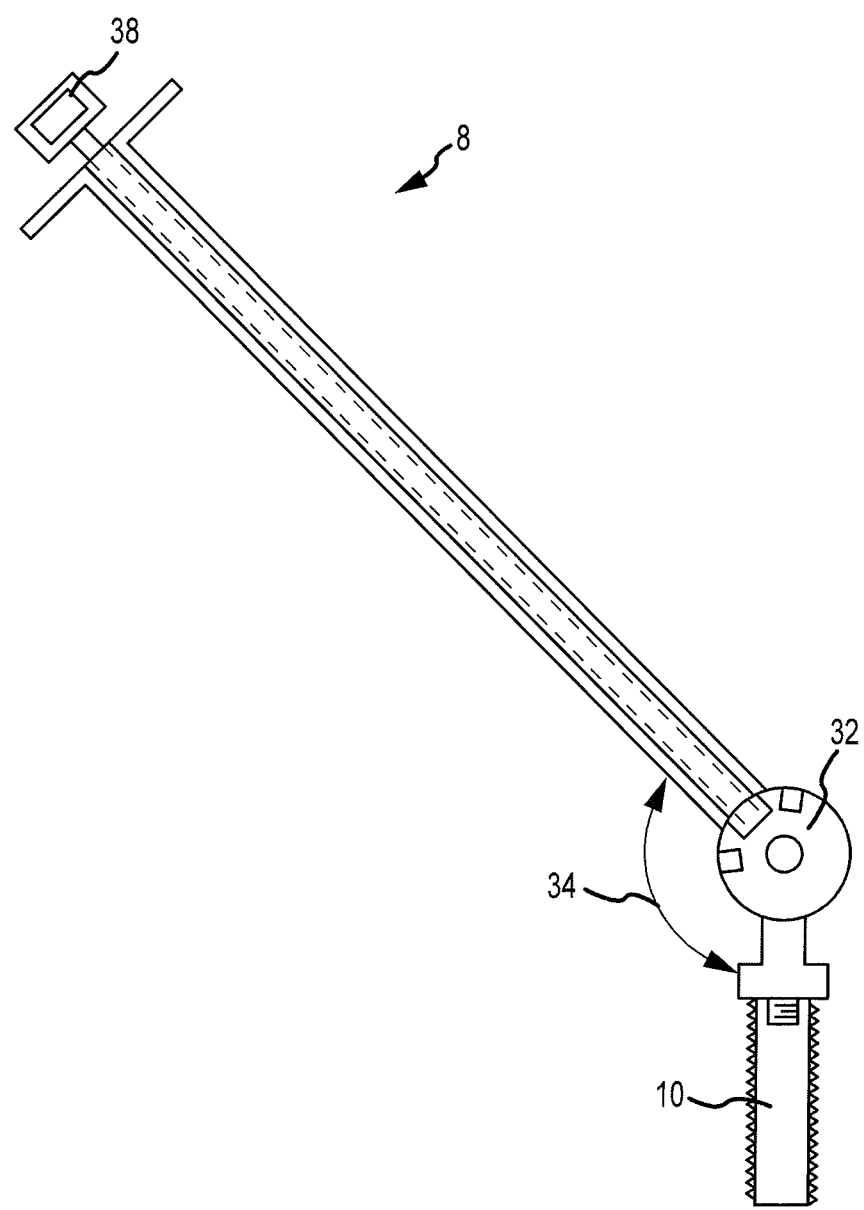
FIG. 9 is a front elevation view of one embodiment of a distraction tool with an adjustable angled head.

Referring now to FIG. 9, a distraction tool 8 with a selectively rotatable distal end feature is provided. The distal end portion has an annular projection or lip 60 that is also offset from the handle portion by an angle. The annular projection or lip 60 serves as a point of contact for a distractor wedge 10, such that when a distractor wedge 10 is being held in place, it contacts the annular projection or lip. In various embodiments, when a distractor wedge 10 is secured to a handle portion 10, the distractor wedge or distal end 10 is tightly contacted with the entire distal face of the annular projection or lip 60. In such embodiments, the annular projection or lip prevents the distraction wedge from moving during placement into the patient. One having ordinary skill in the art will appreciate that the annular lip may have features on the side that engages the wedge 10 to have a stabilizing effect to stabilize the wedge 10 and prevent unwanted rotation or movement of the wedge during its assembly to the distal end and during its release from the distal end. Such a feature may include, for example, a tab, a pin, a ridge, a dowel or an indexing pin. It will be appreciated that the wedge will have a corresponding and complementary feature that engages or is engaged by the feature on the annular lip including, for example, an aperture, an indexing notch, a registration tab or notch, a slot or a groove.

In various embodiments, a distal end of the tool 8 is selectively rotatable. For example, the tool 8 may include an internal member that is configured to rotate about its longitudinal axis when prompted by the user. In such embodiments, the internal member is also configured to releasably secure embodiments of a distal end portion of the tool. The internal member may be a wire, rod or cable that is sized to fit within the inner diameter of the hollow handle and to rotate freely therein, without interference from the inner walls of the handle. The internal member may have, at its proximal end, a means by which the user may releasably secure the wedge 10. In some embodiments, this means is a thumbwheel or thumbscrew 38 that is secured to the distal end of the internal member such that, when the thumb screw 38 is rotated by the user, the internal member rotates about its longitudinal axis. In these embodiments, it is preferable for the thumb screw 38 to be configured so that it may rotate in both directions.

Figure 10:
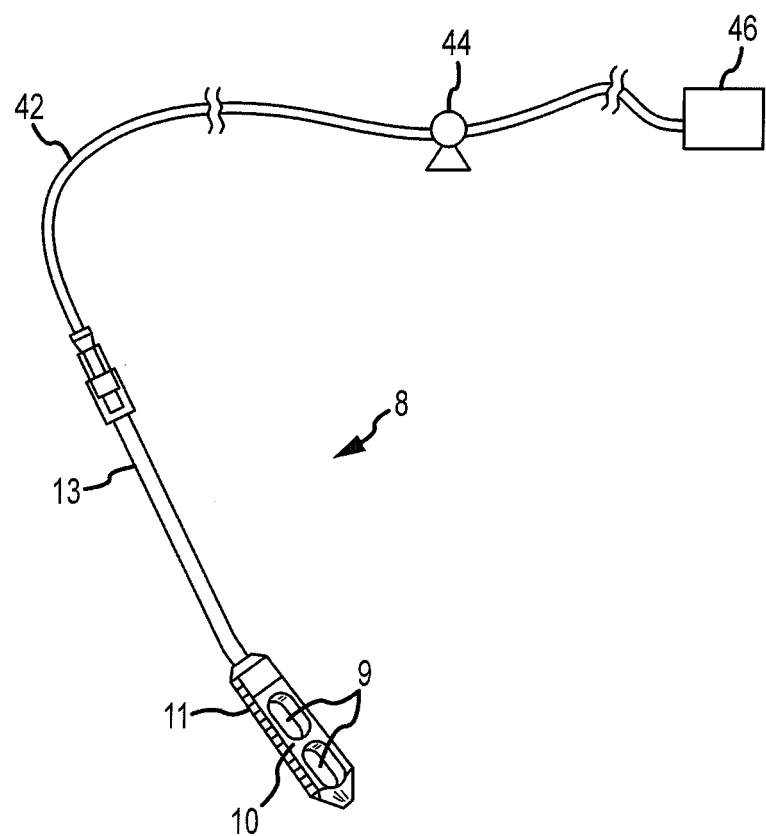
FIG. 10 is a front perspective view of one embodiment of a distraction tool comprising fluid or gas delivery means.

FIG. 10 is a front perspective view of a distraction tool 8 of the present invention comprising fluid delivery systems. As shown, a distraction tool 8 is connected to a conduit or tubing 42 adapted for transmitting a gas or fluid from a pump 44 and/or gas or fluid source 46. A gas or fluid source may comprise any number of known receptacles and sources of fluid including, but not limited to, one or more storage tanks containing various types and quantities of fluid or gas (e.g. medical grade gas or fluid). In various embodiments, a pump 44 is provided for transmitting a gas or fluid to portions of a distractor device 8 at a given pressure. In various embodiments, a user-operable control device (e.g. a trigger mechanism) is provided for selectively directing air to portions of a distractor 8 and a disc space.

As shown in FIGS. 11a, 11b, 11c, 11d embodiments of the present invention comprise a distraction wedge 10 with various textured surfaces 11. In various embodiments, textured surfaces 11 comprise rasps, edges, or protrusions 50 adapted for removing and dislodging material from a disc space. In various embodiments, a series of tools is provided, the series of tools comprising tools with different sized, shaped, and/or oriented rasp features 50. In various embodiments, a single tool comprises multiple different rasp features 50. Rasp features 50 may comprise ridges or protrusions or indentations for imparting and/or displacing material. In alternative embodiments, rasp features 50 comprise a combination of textured features as well as through holes through a portion of a wedge 10 adapted for shearing and trapping of material within a wedge 10.

Features 50 of the present invention may be comprised of various different shapes and comprise indentations, protrusions, or various combinations thereof with respect to at least one surface of the head 10. As shown in FIGS. 11a-d, indentations or protrusions provided on a surgical tool 8 may comprise triangular, square, round, fish scale, diamond, and/or various other shapes as will be recognized by one of ordinary skill in the art. Accordingly, the present invention is not limited to a surgical tool with textured features of a particular dimension or shape.

In various embodiments, a method for preparing an intervertebral workspace is provided. For example, a method comprising the use of at least one distractor tool is provided wherein the distractor tool comprises at least one portion of one surface of a distal end or wedge having textured features adapted for scouring and/or cleaning portions of a workspace (e.g. an endplate). In various embodiments, methods of the present invention further contemplate the use of additional tools, such as various cannulas adapted for use in minimally invasive spinal surgeries. Tools suitable for use in combination with distractor tools as described herein comprise any number of spinal surgery related tools, including, but not limited to, lighting, imaging, and access tools.

In various embodiments, once a distractor tool is inserted and/or positioned into an intervertebral workspace, a user may translate and/or reciprocate the distractor so as to dislodge various materials to be removed from the workspace. In alternative embodiments, distraction may be performed with only a single insertion motion and/or force and a single removal motion and/or force. In embodiments, a vacuum pressure may be applied to a workspace through a distal end of the tool in a continuous manner. In alternative embodiments, vacuum pressure may be selectively applied by a user to a work space through a distal end of the tool.

In various embodiments, a method is provided wherein a distal end of a distractor tool is selectively positioned at a user-desired angle with respect to a longitudinally extending handle portion before use/insertion into a patient.

In various embodiments, a method of spinal distraction is provided comprising a longitudinally extending handle portion selectively attachable to a distal wedge portion. Thus, the appropriate combination of a handle and a distal wedge portion is selected based on, for example, patient size, age, weight, etc., lighting conditions, and/or user preference. Subsequently, the combination is assembled with the handle portion and distal wedge portion being securely attached to one another. The assembled device is then inserted into an intervertebral space so as to prepare a workspace by expanding an intervertebral space upon entrance and remove materials and tissue upon removal. The assembled device may be repeatedly inserted and retractor to achieve the desired expansion and/or cleaning of the disc space. In embodiments, vacuum pressure may be applied to a work space in order to facilitate cleaning of the disc space and/or removal of various materials, such as those dislodged and/or collected by additional features of the distractor tool.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g. the use of disposable components comprising some or all of the apparatus described herein, as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An angled surgical tool for removing tissue from within an intervertebral space, comprising an elongated handle having a proximal end configured to be connected to a tubing for transmitting a gas or fluid from a gas or fluid source and a distal end connected to a shaft, said shaft having a head portion including a distal tip located at a distal terminus of the head portion, said head portion being offset by an angle such that the head portion is angled towards the shaft at an angle ranging from 5 to 45 degrees, the head portion having a top surface consisting of rasp features adapted to remove tissue and debris disposed within a vertebral endplate in an intervertebral space, said top surface being devoid of apertures.

2. The surgical tool of claim 1, wherein said shaft further comprises an internal conduit for conveying a pneumatic pressure through said shaft.

3. The angled surgical tool of claim 1, wherein vacuum pressure is supplied to the shaft, thereby drawing debris toward said shaft distal end.

4. The angled surgical tool of claim 1, wherein a quantity of said fluid or gas is directed through a portion of said tool.

5. The angled surgical tool of claim 1, wherein a positive or negative pressure is transmitted through said shaft.

6. The angled surgical tool of claim 1, wherein said shaft is disposable.

7. The angled surgical tool of claim 1, wherein said shaft is detachably anchored to said head portion.

8. The angled surgical tool of claim 1, wherein said head is detachably anchored to said shaft and wherein the head is disposable.

9. The angled surgical tool of claim 1, wherein said tool facilitates the removal of at least an outer most cell layer of bone to gain access to vascular bone tissues within the intervertebral space.

10. The angled surgical tool of claim 1, wherein said head portion comprises peripheral outer surfaces capable of dislodging, scraping or cutting materials in the intervertebral space.

11. The angled surgical tool of claim 1, wherein said head portion includes flutes for guiding materials that have been dislodged from portions of the intervertebral space.

12. The angled surgical tool of claim 1, wherein said fluid or gas blasts or clears the intervertebral space of debris.

13. The angled surgical tool of claim 1, wherein said fluid comprises one of ambient air, inert gasses, oxygen, water, or saline.

14. The angled surgical tool of claim 1, wherein said head portion is selectively rotatable.

15. The angled surgical tool of claim 1, wherein a quantity of said fluid or gas is directed through a portion of said tool.

16. An angled surgical tool for removing tissue from within an intervertebral space, comprising an elongated handle having a proximal end configured to be connected to a tubing for transmitting a gas or fluid from a gas or fluid source and a distal end connected to a shaft, and said shaft having a head portion including a distal tip located at a distal terminus of the head portion, said head portion being offset by an angle such that the head portion is angled towards the shaft at an angle ranging from 15 to 25 degrees, the head portion having a top surface consisting of rasp features adapted to remove tissue and debris disposed within a vertebral endplate in an intervertebral space, said top surface being devoid of apertures.

17. An angled surgical tool for removing tissue from within an intervertebral space, comprising an elongated handle having a proximal end and a distal end connected to a shaft, said proximal end configured to be connected to a tubing to convey vacuum pressure to the shaft, thereby drawing debris through said shaft, said shaft having a head portion including a distal tip located at a distal terminus of the head portion, said head portion being offset by an angle such that the head portion is angled towards the shaft at an angle ranging from 5 to 45 degrees, the head portion having a top surface consisting of rasp features adapted to remove tissue and debris disposed within a vertebral endplate in an intervertebral space, said top surface being devoid of apertures.

18. The angled surgical tool of claim 17, wherein said head portion is selectively rotatable.

19. The angled surgical tool of claim 17, wherein said head is detachably anchored to said shaft.

20. The angled surgical tool of claim 17, wherein said head is disposable.

* * * * *